United States Patent [19]

Sugimori et al.

[11] Patent Number: 4,684,477
[45] Date of Patent: Aug. 4, 1987

[54] PYRIDINE DERIVATIVES AND THEIR USE IN LIQUID CRYSTALS

[75] Inventors: Shigeru Sugimori, Fujisawashi; Kazunori Nigorikawa; Tetsuya Ogawa, both of Yokohamashi, all of Japan

[73] Assignee: Chisso Corporation, Osaka, Japan

[21] Appl. No.: 833,717

[22] Filed: Feb. 27, 1986

[30] Foreign Application Priority Data

| Mar. 6, 1985 [JP] | Japan | 60-44208 |
| Apr. 8, 1985 [JP] | Japan | 60-74075 |
| Apr. 22, 1985 [JP] | Japan | 60-86121 |
| Jul. 18, 1985 [JP] | Japan | 60-159237 |
| Dec. 20, 1985 [JP] | Japan | 60-287136 |

[51] Int. Cl.[4] ............... C09K 19/34; C09K 19/54; C07D 211/78; C07D 211/72

[52] U.S. Cl. ............... 252/299.61; 252/299.5; 350/350 R; 546/286; 546/301; 546/302; 546/303; 546/290; 546/348; 546/343; 546/345

[58] Field of Search ............... 546/286, 301, 302, 303, 546/290, 348, 343, 345; 252/299.61

[56] References Cited

U.S. PATENT DOCUMENTS 4,533,488  8/1985  Fukui et al. ............... 252/299.61

FOREIGN PATENT DOCUMENTS 163864  8/1985  Japan ............... 546/286

OTHER PUBLICATIONS

Karamysheva et al., Mol. Cryst. Liq. Cryst., 1981, vol. 67, pp. 241-252.
Pavluchenko et al., Advances in Liquid Crystal Research and Applications, 1980, pp. 1007-1013.
Grachev et al., Mol. Cryst. Liq. Cryst., 1981, vol. 65, pp. 133-144.

Primary Examiner—Henry R. Jiles
Assistant Examiner—Robert C. Whittenbaugh
Attorney, Agent, or Firm—Wenderoth, Lind & Ponack

[57] ABSTRACT

A novel pyridine derivative which, when added to liquid crystal substances, can improve various specific features required for the resulting liquid crystal compositions, and a liquid crystal composition containing the same are provided, which pyridine derivative is expressed by the formula

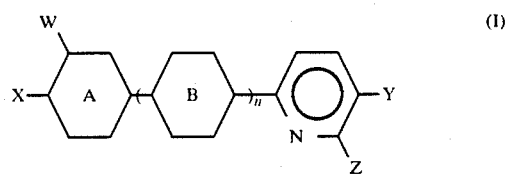

wherein W represents H or F; X, F, Cl or alkyl or alkoxy of 1~10 C;

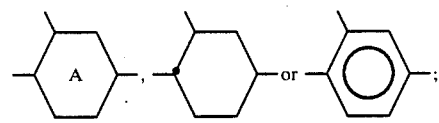

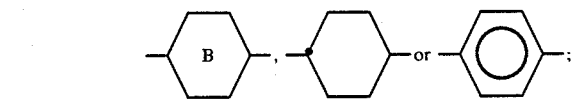

n, 0 or 1; Y, CN or alkyl or alkoxy of 1~10 C; Z, F, Cl or H; and when Z is F or Cl, Y is limited to CN, excluding certain identified compounds.

13 Claims, No Drawings

PYRIDINE DERIVATIVES AND THEIR USE IN LIQUID CRYSTALS

BACKGROUND OF THE INVENTION

This invention relates to a novel compound useful as a component of liquid crystal compositions and a liquid crystal composition containing the same.

Liquid crystal display elements utilize the optical anisotropy and dielectric anisotropy of liquid crystal substances, and are classified into those of various modes such as TN type (twisted nematic type), DS type (dynamic scattering type), guest-host type, DAP type, etc. depending on their display modes; thus the properties of liquid crystal substances suitable to the respective uses thereof are different. All liquid crystal substances, however, are common in that they are to be stable to moisture, air, heat, light, etc. and also those which exhibit a liquid crystal phase within a temperature range as broad as possible and centered around room temperature, have been sought. But it is the present status that there is no single substance which satisfies such conditions; thus liquid crystal compositions obtained by blending several kinds of liquid crystal compounds and if necessary, non-liquid crystal compounds have been used.

In addition to the above-mentioned property that the liquid crystal phases should be present within a temperature range as broad as possible including service temperatures, the following properties have generally been required for liquid crystal compositions used for display elements: low viscosity, superior compatibility with other liquid crystal compositions, low operating threshold voltage, capability to be driven with a small electric power, high operating response velocity, etc.

The object of the present invention is to provide a novel compound which, when added to liquid crystal substances, can improve various specific features required for the resulting liquid crystal compositions, and a liquid crystal composition containing the same.

SUMMARY OF THE INVENTION

The present invention in a first aspect resides in the following main constitution (1) and constitutions (2)~(12) as embodiments thereof:

(1) A pyridine derivative expressed by the formula (I)

wherein W represents H or F; X represents F, Cl or an alkyl group or an alkoxy group each of 1 to 10 carbon atoms;

A represents represents n represents 0 or 1; Y represents CN or an alkyl group or an alkoxy group each of 1 to 10 carbon atoms; Z represents F, Cl or H; and when Z is F or Cl, Y is limited to CN, excluding the case of compounds of the formula (I) wherein W represents H; X, an alkyl group or an alkoxy group each of 1 to 10 carbon atoms;

n, 0; Y, an alkyl group of 1 to 10 carbon atoms or CN; and Z, H.

(2) A 2-substituted-5-cyano-6-chloropyridine according to the above paragraph (1) wherein in said formula (I), W represents H; X, F or Cl;

n, 0 or 1; Y, CN; and Z, Cl.

(3) A 2-substituted-5-cyanopyridine according to the above paragraph (1) wherein in said formula (I), W represents H; X, F or Cl;

n, 0 or 1; Y, CN; and Z, H.

(4) A 2-substituted-5-alkylpyridine according to the above paragraph (1) wherein in said formula (I), W represents H or F; X, F or Cl;

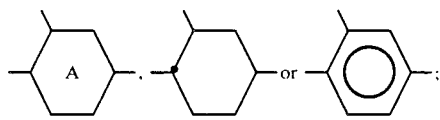

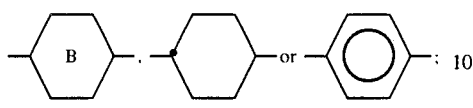

n, 0 or 1; Y, an alkyl group of 1 to 10 carbon atoms; and Z, H.

(5) A 2-substituted-5-alkylpyridine according to the above paragraph (1) wherein W represents H; X, F;

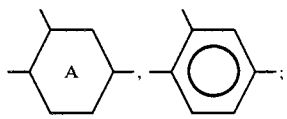

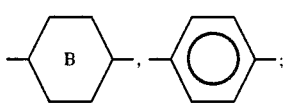

n, 0 or 1; Y, an alkyl group of 1 to 10 carbon atoms; and Z, H.

(6) A 2-substituted-5-alkylpyridine according to the above paragraph (1) wherein in said formula (I), W represents F; X, F;

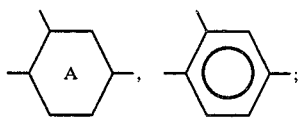

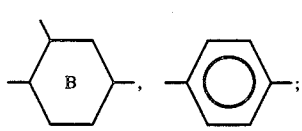

n, 0 or 1; Y, an alkyl group of 1 to 10 carbon atoms; and Z, H.

(7) A 2-substituted-5-cyano-6-chloropyridine according to the above paragraph (1) wherein in said formula (I), W represents H; X, an alkyl group or an alkoxy group each of 1 to 10 carbon atoms;

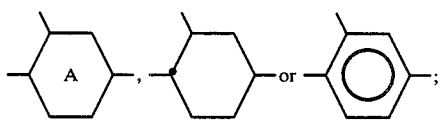

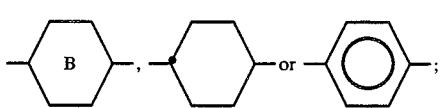

n, 0 or 1; Y, CN; and Z, Cl.

(8) A 2-substituted-5-cyano-6-fluoropyridine according to the above paragraph (1) wherein in said formula (I), W represents H; X, an alkyl group or an alkoxy group each of 1 to 10 carbon atoms;

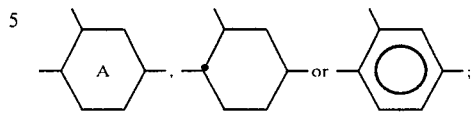

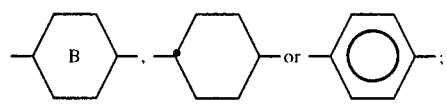

n, 0 or 1; Y, CN; and Z, F.

(9) A 2-substituted-5-cyanopyridine according to the above paragraph (1) wherein in said formula (I), W represents H; X, an alkyl group of 1 to 10 carbon atoms;

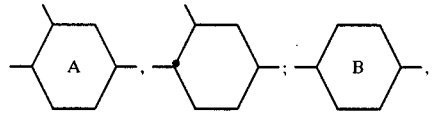

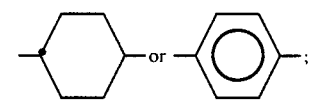

n, 0 or 1; Y, CN; and Z, H.

(10) A 2-substituted-5-substituted-pyridine according to the above paragraph (1) wherein in said formula (I), W represents H; X, an alkyl group or an alkoxy group each of 1 to 10 carbon atoms;

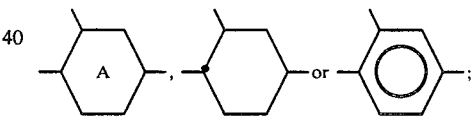

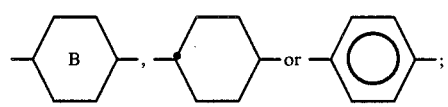

n, 1; Y an alkyl group or an alkoxy group each of 1 to 10 carbon atoms; and Z, H.

(11) A 2-(4-alkylcyclohexyl)-5-alkylpyridine according to the above paragraph (1) wherein in said formula (I), W represents H; X an alkyl group of 1 to 10 carbon atoms;

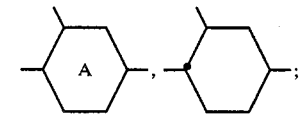

n, 0; Y, an alkyl group of 1 to 10 carbon atoms; and Z, H.

(12) A 2-(4-alkylcyclohexyl)-5-alkoxypyridine according to the above paragraph (1) wherein in said formula (I), W represents H; X, an alkyl group of 1 to 10 carbon atoms;

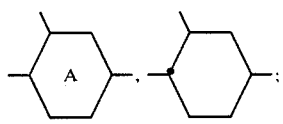

n, 0; Y, an alkoxy group of 1 to 10 carbon atoms; and Z, H.

The present invention in the second aspect resides in a liquid crystal composition having at least two components at least one of which is a pyridine derivative expressed by the formula (I) in the above paragraph (1).

DESCRIPTION OF PREFERRED EMBODIMENTS

The compounds of the present invention may be prepared as follows:

(a) A trans-4-substituted cyclohexyl methyl ketone (II) or a 4'-substituted acetophenone (II) is reacted with a formic acid ester to obtain a sodium enolate of formylacetone derivative (III), which is then condensed with cyanoacetoamide in an aqueous solution of piperidine acetate, to obtain a 3-cyano-6-substituted-2(1)-pyridone (IV), which is treated with phosphorus oxychloride to obtain a 2-substituted-5-cyano-6-chloropyridine (I-a).

(b) The 2-substituted-5-cyano-6-chloropyridine (I-a) obtained in (a) is subjected to a halogen exchange reaction with potassium fluoride to obtain a 2-substituted-5-cyano-6-fluoropyridine (I-b).

(c) The 2-substituted-5-cyano-6-chloropyridine (I-a) obtained in (a) is reduced with Pd-C or zinc powder to obtain a 2-substituted-5-cyanopyridine (I-c).

(d) The 2-substituted-5-cyanopyridine (I-c) obtained in (c) is reacted with a Grignard reagent separately prepared from a halogenated alkyl and Mg to obtain a 2-substituted-5-alkanoylpyridine (V) which is then reduced to obtain a 2-substituted-5-alkylpyridine (I-d).

(e) The 2-substituted-5-alkanoylpyridine (V) obtained in (d) is reacted with a peracid to obtain a 2-subsituted-5-alkanoyloxypyridine N-oxide (VI) which is then reduced and hydrolyzed to obtain a 2-substituted-5-hydroxypyridine (VII), which is then reacted with a halogenated alkyl to obtain a 2-substituted-5-alkoxypyridine (I-e).

Further, compounds of the formula (I) wherein Y represents an alkyl group and Z represents H may also be prepared according to the following preparation method:

(f) To the sodium enolate (III) obtained in (a) is added an aqueous solution of sulfuric acid to obtain a $\beta$-hydroxyvinyl ketone (VIII), which is treated with thionyl chloride to obtain a $\beta$-chlorovinyl ketone (IX), which is reacted with a N-(alkenyl-1)piperidine (X) in the presence of triethylamine, followed by heating the reaction product with perchloric acid to obtain a pyrylium salt (XI), which is then reacted with ammonium acetate to obtain a 2-substituted-5-alkylpyridine (I-f).

The above preparations are expressed by the following reaction equations:

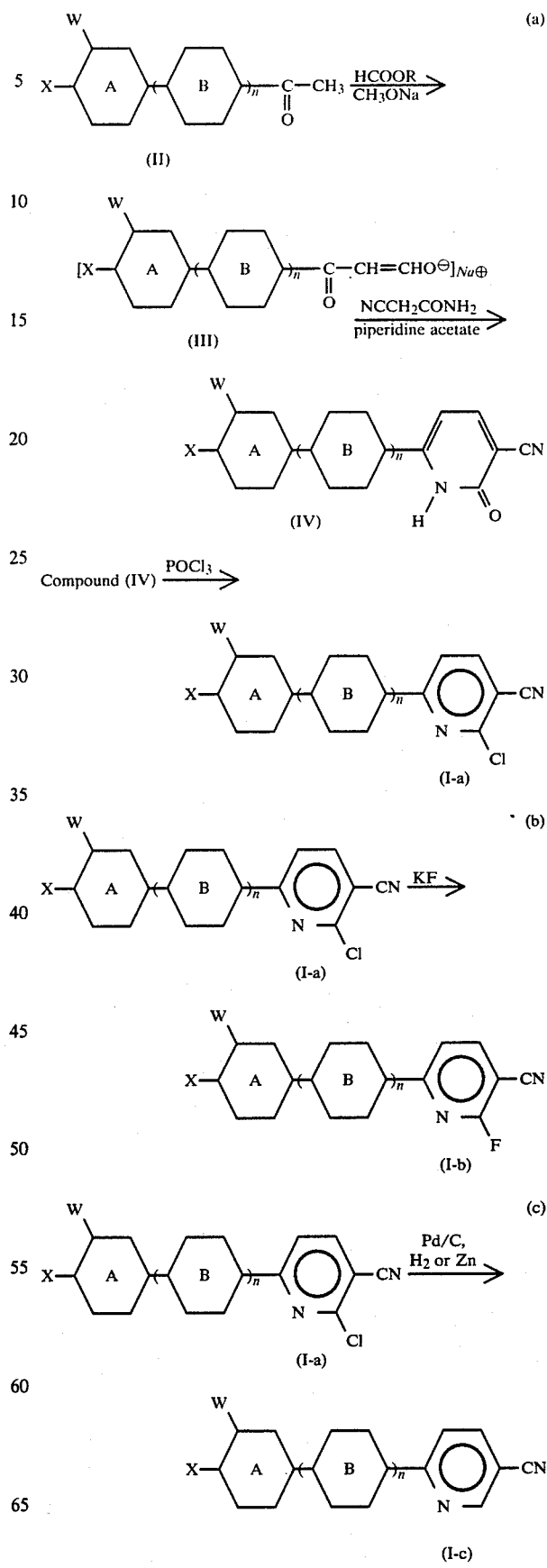

-continued

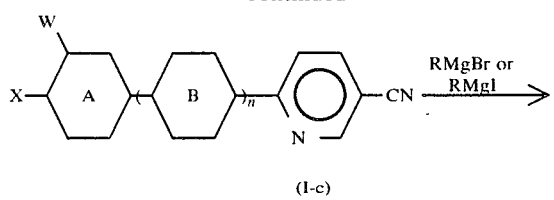

(I-c)

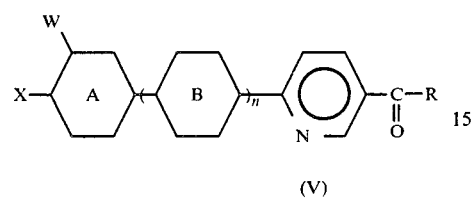

(V)

Compound (V) 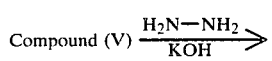

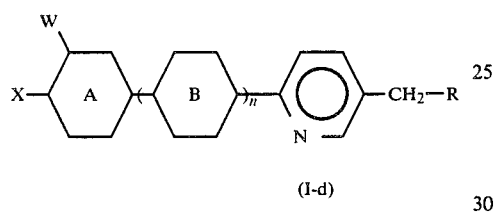

(I-d)

Compound (V) $\xrightarrow{[O]}$

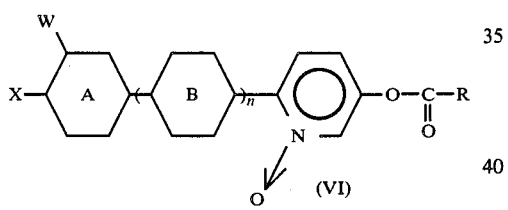

(VI)

Compound (VI) 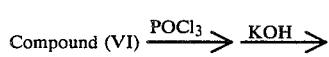

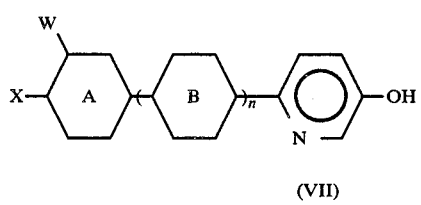

(VII)

Compound (VII) $\xrightarrow{RI}$

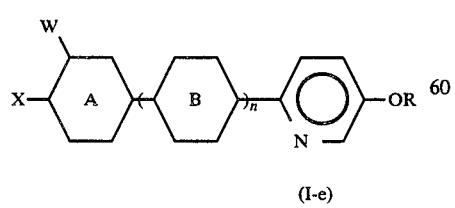

(I-e)

Compound (III) 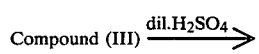

-continued

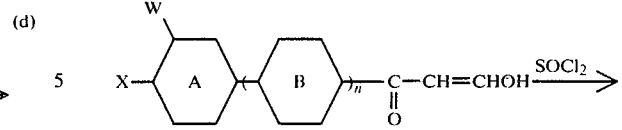

(VIII)

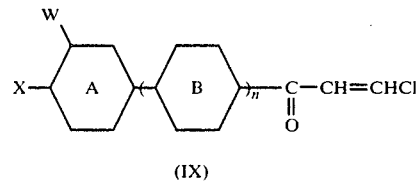

(IX)

Compound (IX) +

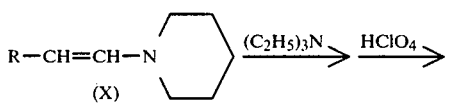

(X)

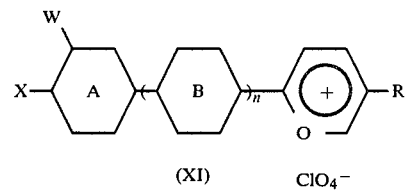

(XI)     ClO$_4^-$

Compound (XI) 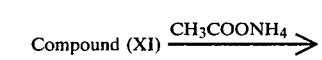

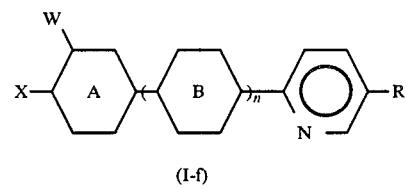

(I-f)

Concrete examples of compounds usable as a component of the liquid crystal composition of the present invention, other than the pyridine derivatives expressed by the formula (I), are liquid crystal compounds of esters such as trans-4-alkylcyclohexanecarboxylic acid-4-alkylphenyl esters, trans-4-alkylcyclohexanecarboxylic acid-4-alkoxyphenyl esters, 4-alkoxybenzoic acid-4-alkylphenyl esters, 4-alkylbenzoic acid-4-cyanophenyl ester, 4-(trans-4-alkylcyclohexyl)benzoic acid-4-cyanophenyl esters, etc., liquid crystal compounds of Schiff's bases such as 4-alkoxybenzylidene-4-alkanoyloxyanilines, 4-alkoxybenzylidene-4-alkylanilines, 4-alkoxybenzylidene-4-cyanoanilines, etc., liquid crystal compounds of biphenyls such as 4'-alkyl-4-cyanobiphenyls, 4'-alkoxy-4-cyanobiphenyls, 4'-alkoxy-4-alkylbiphenyls, etc., compounds of phenylcyclohexanes such as trans-4-alkyl-(4-cyanophenyl)cyclohexanes, trans-4-alkyl-(4 -alkoxyphenyl)cyclohexanes, etc., heterocyclic liquid crystal compounds such as 5-alkyl-2-(4-cyanophenyl)-1,3-dioxanes, 5-alkyl-2-(4-cyanophenyl)pyrimidines, 5-cyano-2-(4-alkylphenyl)pyrimidines, etc.

The content of the compound of the present invention in the composition of the present invention varies depending on the kinds of other components to be mixed. It is usually 1 to 30% by weight, preferably 5 to 15% by weight based on the other components. A concrete example of the composition consists e.g. of 70 to 99% by weight of one kind or a mixture of several kinds of trans-4-alkyl-(4-cyanophenyl)cyclohexanes and 1 to 30% by weight of pyridine derivative(s) of the present invention; preferably 85 to 95% by weight of the former and 5 to 15% by weight of the latter.

Another concrete example of the composition consists of 60 to 84% by weight of one kind or a mixture of several kinds of trans-4-alkyl-(4-cyanophenyl)cyclohexanes, 10 to 15% by weight of one kind or a mixture of several kinds of 4-(trans-4-alkylcyclohexyl)-4'-cyanobiphenyls and 1 to 30% by weight of pyridine derivative(s) of the present invention; preferably 72 to 81% by weight of the former, 12 to 15% by weight of the middle and 5 to 15% by weight of the latter.

The prior art which we consider as most related to the present invention is as follows;

(i) Japanese patent application laid-open No. Sho 60-163864/1985.

(ii) L. A. Karamysheva et al, Mol. Cryst. Liq. Cryst., 67,241 (1981).

(iii) A. I. Pavluchenko et al, Advances in Liquid Crystal Research and Applications, 1007 (1980).

The literature (i) discloses liquid crystal compounds expressed by

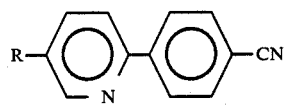

(wherein R represents an alkyl group of 1 to 9 carbon atoms) and

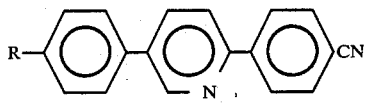

(wherein R represents an alkyl group or an alkoxy group each of 4 to 8 carbon atoms). p The literature (ii) discloses liquid crystal compounds expressed by

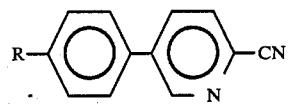

(wherein R represents an alkyl group or an alkoxy group each of 4 to 8 carbon atoms) and

(wherein R represents an alkyl group of 6 or 9).

The literature (iii) discloses liquid crystal compounds expressed by

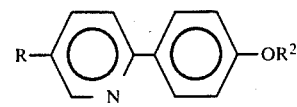

(wherein $R^1$ represents an alkyl group of 4 to 6 carbon atoms and $R^2$ represents an alkyl group of 1, 4, 5, 6 or 7 carbon atoms or an alkanoyl group of 4 or 6 carbon atoms) and

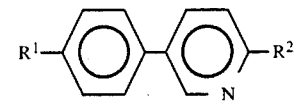

(wherein $R^1$ represents an alkyl group or an alkoxy group each of 4 or 6 carbon atoms and $R^2$ represents an alkyl group of 4, 6 or 9 carbon atoms).

The compounds of the formula (I) of the present invention wherein X represents a halogen or those wherein Y represents CN, when added to a liquid crystal composition, have a great effectiveness of increasing the dielectric anisotropy value (hereinafter abbreviated to $\Delta\epsilon$; $\Delta\epsilon = \epsilon_{\parallel} - \epsilon_{\perp}$ wherein $\epsilon_{\parallel}$ represents a dielectric anisotropy value along the major axis of molecule and $\epsilon_{\perp}$ represents that along the minor axis thereof toward the positive direction). For example, a compound of the formula (I) wherein X represents F;

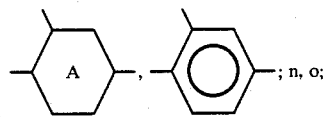

; n, o;

Y, CN; and Z, H, exhibits a contribution to the dielectric anisotropy value to a similar extent to that in the case of a liquid crystal compound having a $\Delta\epsilon$ of about $+41$ in terms of extrapolation value. Further, a compound of the formula (I) having an alkyl group in place of CN group of the above compound, also exhibits a contribution to the dielectric anisotropy value to a similar extent to that in the case of a liquid crystal compound having a $\Delta\epsilon$ of about $+13$ in terms of extrapolation value, and also has a viscosity extrapolation value at 20° C. as extremely small as about 7 cp.

Due to the above-mentioned specific properties, addition of the compound of the present invention as a component of liquid crystal compositions brings about notable effectiveness of reducing the viscosity of the compositions, reducing the threshold voltage of liquid crystal display elements using the compositions and improving the response time.

Among the compounds of the formula (I) of the present invention, those of three rings having H as Z have a high clearing point, and addition thereof has an effectiveness of raising the clearing point of the resulting liquid crystal composition. For example, a compound of the formula (I) wherein W=H, X=n-$C_3H_7$,

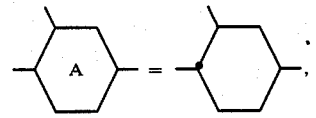

-continued

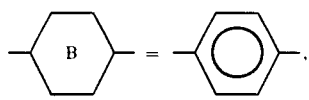

n=1, Y=CN and Z=H exhibits a nematic phase within a temperature range of from 112.6° C. up to 254.0°0 C.; thus as compared with the temperature range (132°~230° C., (U.S. Pat. No. 4,330,426)) of the nematic phase of a compound having benzene ring in place of the pyridine ring of the formula (I), the above compound has a liquid crystal phase having a broad temperature range lower and higher by 20° C. or more both on the lower temperature side and on the higher temperature side.

Further, with regard to TN liquid crystal cell, J. Nehring ("Advances in Liquid Crystal Research and Applications", 1155–1178 (1980)) and G. Baur (Mol. Cryst. Liq. Cryst., 63, 45 (1981)) disclose that in order to make the electrooptic characteristics sharp, it is necessary to 1 make the ratio of $\Delta\epsilon/\epsilon_\perp$ as small as possible and 2 make the ratio of elastic constants $K_{33}/K_{11}$ as small as possible.

A compound of the formula (I) of the present invention wherein W=H, X=alkyl,

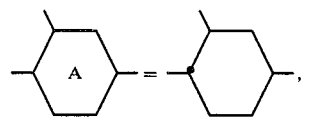

n=0, Y=CN and Z=H is clearly superior in the above points 1 and 2, as compared with a compound having benzene ring in place of the pyridine ring of the formula (I) (U.S. Pat. No. 4,130,502), as shown in Table 1. Further, it is very characteristic that compounds having an alkyl group of even number of carbon atoms and those of odd number of carbon atoms both have a broad temperature range of liquid crystal phase.

TABLE 1

$C_mH_{2m+1}$—⟨ ⟩—Q—CN

Q: ⟨N⟩    Q: ⟨ ⟩

| | Present invention (°C.) | | | | U.S. Pat. No. 4,130,520 (°C.) | | |
|---|---|---|---|---|---|---|---|
| m | M.P. | Clearing point | $\Delta\epsilon/\epsilon_\perp$ | $K_{33}/K_{11}$ | M.P. | Clearing point | $\Delta\epsilon/\epsilon_\perp$ | $K_{33}/K_{11}$ |
| 3 | 47.6 | 51.9 | 0.98 | 1.60 | 42 | 45 | 1.97 | 1.70 |
| 4 | 35.0 | 52.0 | 0.72 | | 41 | (39) | 1.66 | |
| 5 | 48.2 | 64.1 | 1.11 | | 30 | 55 | 1.90 | |
| 6 | 33.2 | 61.2 | 0.72 | | 42 | 47 | — | |

In the above Table, $\Delta\epsilon$ and $\epsilon_\perp$ refer to extrapolation values from the dielectric constants obtained by sealing a liquid crystal composition consisting of 15 parts by weight of the respective compounds in the above Table and 85 parts by weight of the following liquid crystal composition into a TN cell of 10 μm thickness, followed by measurement at 25° C.:

| | |
|---|---|
| Trans-4-propyl-(4-cyanophenyl)cyclohexane | 30% by weight, |
| Trans-4-pentyl-(4-cyanophenyl)cyclohexane | 40% by weight and |
| Trans-4-heptyl-(4-cyanophenyl)cyclohexane | 30% by weight. |

The present invention will be described in more detail by way of Examples, but it should not be construed to be limited thereto.

EXAMPLE 1

2-(4-Fluorophenyl)-4-cyano-6-chloropyridine

A mixed solution of 4'-fluoroacetophenone (28.4 g) with ethyl formate (15.3 g) was dropwise added to a suspension of sodium methoxide (11.2 g) in toluene (200 ml), followed by reacting the mixture at room temperature for 8 hours, thereafter adding water (250 ml), adding to the separated aqueous layer, cyanoacetamide (17.4 g) and piperidine acetate (4 g), refluxing the mixture for 5 hours, cooling, thereafter adding acetic acid till the resulting material became an acidic solution, and filtering off and drying the resulting precipitates to obtain 3-cyano-6-(4-fluorophenyl)-2(1)-pyridone (22.5 g), which was heated with phosphorus oxychloride (100 ml) for 8 hours, distilling off phosphorus oxychloride, adding the residue to warm water (100 ml), thereafter adding 2N aqueous solution of NaOH till the solution became alkaline, adding toluene (200 ml) to the resulting solution to extract the product, washing the separated toluene layer with water till the washing water became neutral, distilling off the solvent from the toluene layer and recrystallizing the residue from ethyl acetate to obtain the objective 2-(4-fluorophenyl)-5-cyano-6-chloropyridine (17.4 g). M.P.: 177.5° C.

EXAMPLES 2–10

Example 1 was repeated except that 4'-fluoroacetophenone of Example 1 was replaced by other 4'-substituted acetophenones or trans-4-substituted cyclohexyl methyl ketones, to prepare compounds shown in Examples 2–10 in Table 2. The values of physical properties thereof are shown in Table 2 together with the results of Example 1.

TABLE 2
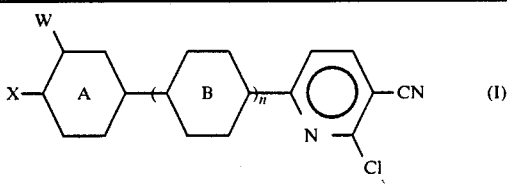
| Example | W | X | A | n | B | Phase transition point (°C.) C | S | N | I |
|---|---|---|---|---|---|---|---|---|---|
| 1 | H | F | phenyl | 0 | | . 177.5 | | | . |
| 2 | H | C₂H₅ | phenyl | 0 | | . 105.6 | | | . |
| 3 | H | n-C₃H₇ | phenyl | 0 | | . 83.4 | | | . |
| 4 | H | n-C₄H₉ | phenyl | 0 | | . 106.7 | | | . |
| 5 | H | n-C₅H₁₁O | phenyl | 0 | | . 76.8 | | | . |
| 6 | H | n-C₃H₇ | cyclohexyl | 0 | | . 29.5 | | | . |
| 7 | H | n-C₅H₁₁ | cyclohexyl | 0 | | . 71.3 | | | . |
| 8 | H | n-C₇H₁₅ | cyclohexyl | 0 | | . 46.3 | | | . |
| 9 | H | n-C₃H₇ | cyclohexyl | 1 | phenyl | . 109.4 | | . 120.7 | . |

TABLE 2-continued structure: X—A—(B)n—pyridine(with W substituent)—CN, Cl (formula I)

In formula (I)

| Example | W | X | A | n | B | Phase transition point (°C.) C S N I |
|---|---|---|---|---|---|---|
| 10 | H | n-C₃H₇ | cyclohexyl | 1 | cyclohexyl | · 105.3   · 124.8   · |

In the above Table, C, S, N and I respectively represent crystalline, smectic, nematic and isotropic liquid phases, and the symbol · therebelow indicates that the above phases are present, and the numeral figures are transition points (°C.) from the phase thereabove to the phase on the right side thereof.

EXAMPLE 11

2-(4-Fluorophenyl)-5-cyanopyridine 2-(4-Fluorophenyl)-5-cyano-6-chloropyridine (8.6 g) prepared in Example 1 was dissolved in ethyl acetate (300 ml), followed by adding to the solution, Pd-C (1 g) and triethylamine (12 ml), subjecting the above pyridine derivative to catalytic reduction at ordinary temperature and ordinary pressure, thereafter adding water (100 ml), filtering, withdrawing the ethyl acetate layer separated from the filtrate, twice washing it with water, distilling off ethyl acetate, and recrystallizing the residue from ethanol to obtain the objective 2-(4-fluorophenyl)-5-cyanopyridine (3.8 g). M.P.: 149.0° C.

EXAMPLE 12

2-(Trans-4-n-propylcyclohexyl)-5-cyanopyridine

2-Ethoxyethanol (200 ml), water (40 ml), and zinc powder (20 g) were added to 2-(trans-4-n-propylcyclohexyl)-5-cyano-6-chloropyridine (17.0 g) of Example 6, followed by heating the mixture under reflux for 28 hours, cooling, thereafter filtering, adding toluene (200 ml) and water (500 ml) to the filtrate, stirring, still standing, separating the toluene layer, twice washing it with water, and carrying out the same procedure as in Example 11 to obtain the objective 2-(trans-4- n-propylcyclohexyl)-5-cyanopyridine (5 g). C-N point: 47.6° C. N-I point: 51.9° C.

EXAMPLES 13–19

Examples 11 and 12 were repeated except that 2-(4-fluorophenyl)-5-cyano-6-chloropyridine in Example 11 and 2-(trans-4-n-propylcyclohexyl)-5-cyano-6-chloropyridine in Example 12 were respectively replaced by other 2-substituted-5-cyano-6-chloropyridines, to prepare compounds shown in Examples 13–19 in Table 3. The values of physical properties thereof are shown in Table 3 together with the results of Examples 11 and 12.

TABLE 3 structure: X—A—(B)n—pyridine(with W substituent)—CN (formula I)

In formula (I)

| Example | W | X | A | n | B | Phase transition point (°C.) C S N I |
|---|---|---|---|---|---|---|
| 11 | H | F | phenyl | 0 | — | · 149.0   · |

TABLE 3-continued

Structure (I):

W–[A]–[B]ₙ–[pyridine with N]–CN, with X on A

| Example | W | X | A | n | B | Phase transition point (°C) C | S | N | I |
|---|---|---|---|---|---|---|---|---|---|
| 12 | H | n-C₃H₇ | cyclohexane | 0 | — | • 47.6 | | • 51.9 | • |
| 13 | H | C₂H₅ | cyclohexane | 0 | — | • 29.2 | | | • |
| 14 | H | n-C₄H₉ | cyclohexane | 0 | — | • 35.0 | | • 52.0 | • |
| 15 | H | n-C₅H₁₁ | cyclohexane | 0 | — | • 48.2 | | • 64.1 | • |
| 16 | H | n-C₆H₁₃ | cyclohexane | 0 | — | • 33.2 | • 42.3 | • 61.2 | • |
| 17 | H | n-C₇H₁₅ | cyclohexane | 0 | — | • 50.7 | • 53.3 | • 67.2 | • |
| 18 | H | n-C₃H₇ | cyclohexane | 1 | phenyl | • 112.6 | | • 254.6 | • |
| 19 | H | n-C₃H₇ | cyclohexane | 1 | cyclohexane | • 88.5 | • 102.7 | • 245.2 | • |

EXAMPLE 20

2-(4-Fluorophenyl)-5-n-pentylpyridine

A solution of 2-(4-fluorophenyl)-5-cyanopyridine (3.1 g) of Example 11 in tetrahydrofuran (30 ml) was added to a tetrahydrofuran solution (50 ml) of a Grignard reagent prepared from metallic Mg (0.6 g) and n-butyl iodide (4.4 g), followed by reacting the mixture at 60° C. for 5 hours, pouring the resulting solution in cooled 2N-HCl aqueous solution (100 ml), adding 2N-NaOH aqueous solution to make the solution alkaline, adding toluene (200 ml) to the solution, withdrawing the separated toluene layer, washing it with water till the washing water became neutral, distilling off toluene from the toluene layer and recrystallizing the residue from ethanol to obtain 2-(4-fluorophenyl)-5-valeroylpyridine (1.8 g) having a m.p. of 104.4° C. To this compound were added hydrazine hydrate (4 g), diethylene glycol (20 ml) and KOH (2.2 g), followed by agitating the mixture at 110° C. for one hour and further at 200° C. for 3 hours, cooling, adding chloroform (100 ml), washing the separated chloroform layer with water till the washing water became neutral, distilling off the solvent from the chloroform solution and distilling the residue to obtain the objective 2-(4-fluorophenyl)-5-n-pentylpyridine (0.3 g). B.P.: 152.0° C./2 mmHg. M.P.: 27.0° C.

EXAMPLES 21–27

The compounds shown in Examples 21–27 in Table 4 were prepared by repeating Example 20 except that 2-(4-fluorophenyl)-5-cyanopyridine of Example 20 was replaced by other 2-substituted-5-cyanopyridines according to the above-mentioned preparation method (f). The value of physical properties thereof are shown in Table 4 together with the results of Example 20.

TABLE 4

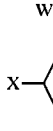

(I)

| | | | In formula (I) | | | | Phase transition point (°C.) | | | |
|---|---|---|---|---|---|---|---|---|---|---|
| Example | W | X | A | n | B | Y | B.P. (°C./mmHg) | C | S | N | I |
| 20 | H | F | 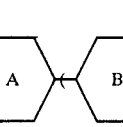 | 0 | | n-C$_5$H$_{11}$ | 152.5/2 | • 27.0 | | | • |
| 21 | H | F |  | 0 | | C$_2$H$_5$ | 120.0/2 | • 27.0 | | | • |
| 22 | H | F | 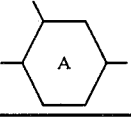 | 0 | | n-C$_3$H$_7$ | 128.0/2 | • 20.4 | | | • |
| 23 | H | F | 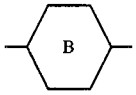 | 0 | | n-C$_4$H$_9$ | 138.5/2 | • 19.8 | | | • |
| 24 | F | F |  | 0 | | n-C$_5$H$_{11}$ | 152.0/2 | • 14.3 | | | • |
| 25 | H | n-C$_3$H$_7$ | 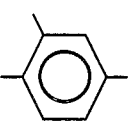 | 0 | | n-C$_5$H$_{11}$ | 161.0/2 | | | | |
| 26 | H | F |  | 1 |  | n-C$_5$H$_{11}$ | | • 128.1 | • 199.5 | | • |

TABLE 4-continued

Formula (I): X—[A]ₙ—[B]—[pyridine]—Y, with W substituent on A

| Example | W | X | (A) | n | (B) | Y | B.P. (°C./mmHg) | C | S | N | I |
|---|---|---|---|---|---|---|---|---|---|---|---|
| 27 | H | $C_2H_5$ | cyclohexyl | 1 | phenyl | n-$C_5H_{11}$ | | • 124.1 | • 150.0 | • 187.6 | • |

EXAMPLE 28

2-(Trans-4-n-hexylcyclohexyl)-5-ethoxypyridine

An ethyl ether solution (30 ml) of 2-(trans-4-n-hexylcyclohexyl)-5-cyanopyridine (13.2 g) of Example 16 was added to an ethyl ether solution (50 ml) of a Grignard reagent prepared from metallic Mg (2.5 g) and butyl bromide (13.8 g), followed by agitating the mixture at 35° C. for 5 hours, pouring the resulting solution in ice water containing 6N-HCl aqueous solution (100 ml), adding 2N-NaOH aqueous solution till the solution became basic, adding toluene (300 ml) to the resulting solution, washing the separated organic layer with water till the washing water became neutral, distilling off the solvent, and recrystallizing the residue from methanol to obtain 2-(trans-4-n-hexylcyclohexyl)-5-valeroylpyridine (4.3 g). This compound exhibited smectic phase between 46° C. and 66° C. To this compound were added m-chloroperbenzoic acid (4.6 g) and chloroform (50 ml), followed by agitating the mixture at room temperature for one week, filtering off the resulting precipitates, adding phosphorus oxychloride (10 ml) and toluene (50 ml) to the precipitates, heating the mixture at 80° C. for 2 hours, distilling off the solvent, adding warm water (100 ml), adding 2N-NaOH aqueous solution till the solution became basic, adding toluene (100 ml), washing the separated organic layer with water till the washing water became neutral, and distilling off the solvent to obtain 2-(trans-4-n-hexylcyclohexyl)-5-valeroyloxypyridine. To this compound were added KOH (1.5 g) and ethylene glycol (50 ml), followed by heating the mixture at 150° C. for 8 hours, cooling, adding water (100 ml), adding acetic acid till the solution became acidic, filtering off the resulting precipitates, and recrystallizing from methanol to obtain 2-(trans-4-n-hexylcyclohexyl)-5-hydroxypyridine. This compound was dissolved in ethanol (30 ml), followed by adding ethyl iodide (1.0 g), KOH (0.3 g) and water (2 ml), heating the mixture at 65° C. for 5 hours, cooling, adding water (100 ml) and toluene (50 ml), washing the separated organic layer with water till the washing water became neutral, and distilling off the solvent from the organic layer to obtain the objective 2-(trans-4-n-hexylcyclohexyl)-5-ethoxypyridine.

EXAMPLE 29 (APPLICATION EXAMPLE)

A liquid crystal composition (A) consisting of (A) {
trans-4-propyl-(4-cyanophenyl)cyclohexane — 30% by weight,
trans-4-pentyl-(4-cyanophenyl)cyclohexane — 40% by weight and
trans-4-heptyl-(4-cyanophenyl)cyclohexane — 30% by weight
} had a N-I point of 52.1° C. and a viscosity at 20° C. of 23.4 cp. When this liquid crystal composition was sealed in a TN cell of 10 μm, the operating threshold voltage and saturation voltage were 1.54 V and 2.13 V, respectively. A liquid crystal composition obtained by adding 5 parts by weight of 2-(4-fluorophenyl)-5-cyanopyridine of Example 11 as a compound of the present invention to 95 parts by weight of the above liquid crystal composition (A) had a N-I point of 51.2° C. and a viscosity at 20° C. of 23.5 cp. When this liquid crystal composition was sealed in the above TN cell, the operating threshold voltage and saturation voltage were 1.50 V and 2.05 V, respectively. This shows that addition of the compound of the present invention reduces the operating voltages almost without lowering the clearing point and also almost without increasing the viscosity.

EXAMPLES 30–35 (APPLICATION EXAMPLES)

To 85 parts by weight of the liquid crystal composition (A) of Example 25 were added 15 parts by weight of the respective compounds of Examples 12–17 of the present invention. The resulting respective liquid crystal compositions were sealed in the above TN cell, and the dielectric constants of the respective compounds sought by extrapolation from the dielectric constants measured as above are shown in Table 5.

TABLE 5

X—[cyclohexyl]—[pyridine]—CN

| | | Dielectric constant 25° C. | | |
|---|---|---|---|---|
| Example | X | $\epsilon_\parallel$ | $\epsilon_\perp$ | $\Delta\epsilon$ |
| 30 | $C_2H_5$ | 19.9 | 12.0 | +7.9 |
| 31 | n-$C_3H_7$ | 17.2 | 8.7 | +8.5 |
| 32 | n-$C_4H_9$ | 17.2 | 10.0 | +7.2 |
| 33 | n-$C_5H_{11}$ | 22.6 | 10.7 | +11.9 |
| 34 | n-$C_6H_{13}$ | 13.9 | 8.0 | +5.9 |

TABLE 5-continued

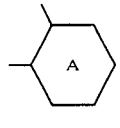

| | | Dielectric constant 25° C. | | |
|---|---|---|---|---|
| Example | X | ε∥ | ε⊥ | Δε |
| 35 | n-C₇H₁₅ | 17.9 | 9.4 | +8.5 |

EXAMPLE 36 (APPLICATION EXAMPLE)

A liquid crystal composition (B) consisting of

| (B) | trans-4-propyl-(4-cyanophenyl)cyclohexane | 24% by weight, |
|---|---|---|
| | trans-4-pentyl-(4-cyanophenyl)cyclohexane | 36% by weight, |
| | trans-4-heptyl-(4-cyanophenyl)cyclohexane | 25% by weight and |
| | trans-4-pentyl-(4'-cyanobiphenylyl-4)cyclohexane | 15% by weight | had a nematic mesomorphic range of −5° C.∼ +72.0° C. and a viscosity at 20° C. of 27.8 cp. When this liquid crystal composition was sealed in the above TN cell, the operating threshold voltage and saturation voltage were 1.75 V and 2.40 V, respectively. A nematic liquid crystal composition obtained by adding 15 parts by weight of 2-(4-fluorophenyl)-5-pentylpyridine of Example 20 as a compound of the present invention to 85 parts by weight of the above liquid crystal composition (B) had a mesomorphic range of −12° C. to +54.5° C., that is, the temperature region on the low temperature side was improved. Further, the viscosity at 20° C. was 24.7 cp, that is, it was improved to a large extent. Further, when the composition was sealed in the above TN cell, the operating threshold voltage and saturation voltage were 1.41 V and 1.90 V, respectively, that is, both the voltages lowered to a large extent.

EXAMPLE 37 (APPLICATION EXAMPLE)

A liquid crystal composition obtained by adding 15 parts by weight of 2-(trans-4-n-propylcyclohexyl)-5-n-pentylpyridine of Example 25 as a compound of the present invention to 85 parts by weight of the liquid crystal composition (B) of Example 36, had a N-I point of 47.3° C. and a viscosity at 20° C. of 24.0 cp. When this liquid crystal composition was sealed in the above TN cell, the operating threshold voltage and saturation voltage were 1.34 V and 1.83 V, respectively. These facts show that addition of the compound of the present invention improves the viscosity and reduces the operating voltages.

As described above, by using the compounds of the present invention, it is possible to improve the characteristics of liquid crystal compositions with great effectiveness.

What we claim is:

1. A pyridine derivative expressed by the formula

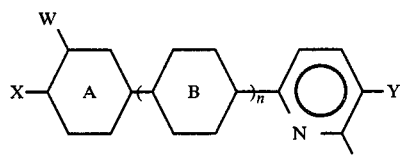

(I)

wherein W represents H or F; X represents F, Cl or an alkyl group or an alkoxy group each of 1 to 10 carbon atoms;

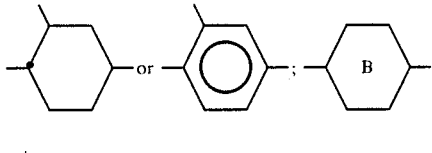

represents

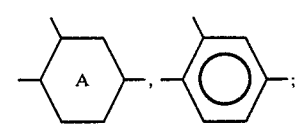

n represents 0 or 1; Y represents CN or an alkyl group or an alkoxy group each of 1 to 10 carbon atoms; Z represents F, Cl or H; and when Z is F or Cl, Y is limited to CN, excluding the case of compounds of the formula (I) wherein W represents H; X, an alkyl group or an alkoxy group each of 1 to 10 carbon atoms;

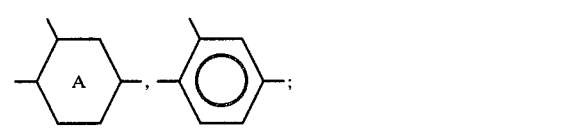

n, O; Y, an alkyl group of 1 to 10 carbon atoms or CN; and Z,H.

2. A pyridine derivative according to claim 1 wherein in said formula (I), W represents H; X, F or Cl; Y, CN; and Z, Cl.

3. A pyridine derivative according to claim 1 wherein in said formula (I), W represents H; X, F or Cl; Y, CN; and Z, H.

4. A pyridine derivative according to claim 1 wherein in said formula (I), X represents F or Cl; Y, an alkyl group of 1 to 10 carbon atoms; and Z, H.

5. A pyridine derivative according to claim 1 wherein in said formula (I), W represents H; X, F;

Y, an alkyl group of 1 to 10 carbon atoms; and Z, H.

6. A pyridine derivative according to claim 1 wherein in said formula (I), W and X both represent F;

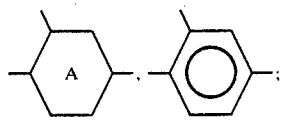

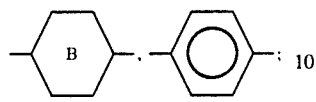

Y, an alkyl group of 1 to 10 carbon atoms; and Z, H.

7. A pyridine derivative according to claim 1 wherein in said formula (I), W represents H; X, an alkyl group or an alkoxy group of each of 1 to 10 carbon atoms; Y, CN; and Z, Cl.

8. A pyridine derivative according to claim 1 wherein in said formula (I), W represents H; X, an alkyl group or an alkoxy group each of 1 to 10 carbon atoms; Y, CN; and Z, F.

9. A pyridine derivative according to claim 1 wherein in said formula (I), W represents H; X, an alkyl group of 1 to 10 carbon atoms;

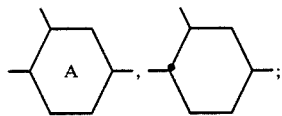

Y, CN; and Z, H.

10. A pyridine derivative according to claim 1 wherein in said formula (I), W represents H; X, an alkyl group or an alkoxy group each of 1 to 10 carbon atoms; n, 1; Y, an alkyl group or an alkoxy group each of 1 to 10 carbon atoms; and Z, H.

11. A pyridine derivative according to claim 1 wherein in said formula (I), W represents H; X and Y both, an alkyl group of 1 to 10 carbon atoms;

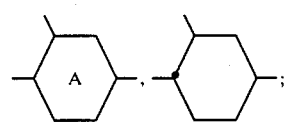

n, O; and Z, H.

12. A pyridine derivative according to claim 1 wherein in said formula (I), W represents H; X, an alkyl group of 1 to    carbon atoms;

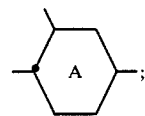

n, O; Y, an alkoxy group of 1 to 10 carbon atoms; and Z, H.

13. A liquid crystal composition having at least two components at least one of which is a pyridine derivative expressed by the formula (I) as set forth in claim 1.

* * * * *